United States Patent
Wimmer

Patent Number: 5,275,582
Date of Patent: Jan. 4, 1994

[54] DISPOSABLE SYRINGE

[76] Inventor: Erwin Wimmer, Thurnsdorf 3, A-4300 St. Valentin, Austria

[21] Appl. No.: 961,443

[22] Filed: Oct. 15, 1992

[30] Foreign Application Priority Data

Oct. 22, 1991 [AT] Austria ................. 2102/91

[51] Int. Cl.$^5$ .............................................. A61M 5/00
[52] U.S. Cl. ..................................... 604/218; 604/222
[58] Field of Search ............... 604/218, 187, 110, 221, 604/222, 228, 256, 229, 230

[56]  References Cited

U.S. PATENT DOCUMENTS 4,704,105  11/1987  Adorjan et al. ................. 604/221 X

FOREIGN PATENT DOCUMENTS

| 2025379 | 12/1971 | Fed. Rep. of Germany . |
| 1104570 | 6/1955 | France ................. 604/218 |
| 1228933 | 9/1960 | France . |
| 1500009 | 5/1966 | France . |
| 2264562 | 3/1974 | France ................. 604/218 |
| 366126 | 1/1963 | Switzerland . |

Primary Examiner—John D. Yasko
Attorney, Agent, or Firm—Kurt Kelman

[57]  ABSTRACT

A disposable syringe comprises a syringe cylinder and a syringe piston. The syringe cylinder is open at one end and at its other end has an end wall, which is closed with the exception of a region adjacent to a needle holder. The syringe piston comprises a piston skirt, which protrudes from the syringe cylinder, and a piston head, which is disposed within the syringe cylinder and provided with an annular seal. The annular seal is connected to the piston head by an annular peripheral flange.

In order to provide a syringe which can easily be actuated and is nevertheless absolutely tight, the flange is frustoconical and flares toward the piston skirt. The radial distance from the inside peripheral surface of the hollow frustoconical flange to the piston skirt increases continuously. The flange is adjoined by the annular seal, which consists of a coaxial cylinder and freely protrudes on the side of the piston head.

3 Claims, 2 Drawing Sheets

DISPOSABLE SYRINGE

BACKGROUND OF THE INVENTION

1. Field of the Invention

This invention relates to a disposable syringe comprising a syringe cylinder and a syringe piston, wherein the syringe cylinder is open at one end and at the other end has an end wall, which is closed with the exception of a region adjacent to a needle holder, and the syringe piston comprises a piston skirt, which has a free end that protrudes from the syringe cylinder and at that free end carries a handle, and said piston also comprises a piston head, which is disposed within the syringe cylinder and is provided with an annular seal, which contacts the inside surface of the cylinder and is connected to the piston head by a peripheral annular flange.

2. Description of the Prior Art

Such disposable syringes are generally made of plastic and are intended to ensure an absolutely tight contact between the annular seal and the inside surface of the cylinder during the intake and delivery strokes of the piston and to permit the piston to be actuated gently and with a minimum of force during the actual injection. These two requirements are not satisfactorily met by the existing disposable syringes, in which the annular seals consist of sealing beads integrally formed on the piston head or of flanges provided with two-legged sealing lips (Published German Application 20 25 379; French Patent Specification 15 00 009) so that the seal proper is supported by means which are rather stiff in a radial direction and a sufficiently strong pressure force is exerted between the seal and the inside surface of the cylinder. But that design has a result that the cylinder wall will expand during a storage of the syringe for considerable time so that the sealing action is more or less lost and it is no longer possible to actuate the piston as uniformly as is desired because the strain has resulted in a variation of the diameter of the cylinder. That situation cannot be improved even by a closer fit between the seal and the inside surface of the cylinder because this would result only in a requirement for a stronger force for actuating the piston so that a sensible actuation of the piston would no longer be possible. It has been attempted to eliminate that disadvantage by an incorporation of a solid lubricant in the material of the cylinder. But in that case a long time must be permitted to elapse after the manufacture of the syringe before said solid lubricant emerges from the material for a lubricating action.

In other known syringes the piston head is caplike and fitted on the adapter end of the piston skirt (Swiss Patent Specification 366,126; French Patent Specification 1,228,933) and constitutes a protruding conical sealing lip because its peripheral surface defines a forwardly open annular wedge-shaped gap and said sealing lip is integrally formed with an oppositely directed, second sealing lip. In order to ensure the required tightness in both directions in which the piston is actuated, the sealing lips must contact the inside surface of the cylinder under a sufficiently strong pressure force so that the seal has a high stiffness, with all the disadvantages involved therein. That stiffness is further increased by the fact that the piston head must be sufficiently firmly fitted on the piston skirt.

All said known disposable syringes also involve the risk that a leak may result from a canting of the piston as the syringe is actuated. Such a canting cannot be prevented because there is a radial clearance between the piston skirt and the syringe cylinder and because the syringe is made of flexible material.

SUMMARY OF THE INVENTION

For this reason it is an object of the invention to eliminate said disadvantages and to provide a disposable syringe which is of the kind described first hereinbefore and distinguishes in that it can be actuated with ease and that it is absolutely tight.

That object is accomplished in accordance with the invention in that the flange has a frustoconical outside surface, which faces the inside surface of said syringe cylinder and said end wall of said syringe cylinder, and a frustoconical inside surface, which faces said piston skirt and said open end of said syringe cylinder, said flange flares toward said open end of said syringe cylinder, the radial clearance between said frustoconical inside surface and the piston skirt increases continuously, and the annular seal is cylindrical and is joined to and coaxial to said flange and freely protrudes toward said end wall. Owing to said shapes of the flange and the annular seal, the seal is relatively softly supported in a radial direction and a resilient sealing system is provided so that the biasing forces being exerted will be very weak and an expansion of the syringe cylinder need not be feared even during a prolonged storage and, besides, the reciprocation of the syringe piston in the syringe cylinder will involve only low frictional forces and for this reason can be effected by a small actuating force. The conical shape of the flange and the provision of the unsupported and freely protruding portion of the annular seal will ensure a compliance and resiliency in a radial direction so that the syringe can be actuated as easily as is desired and the syringe is absolutely tight. Owing to the special shapes of the flange and the seal the pressure conditions existing in the cylinder space will influence the sealing forces and will ensure that the pressure force under which the seal must contact the inside surface of the cylinder will match said pressure conditions. Any expansion of the syringe cylinder or any canting of the piston can easily be compensated owing to the resilience of the seal of the piston without any risk of a leak.

The compliance and resiliency of the means for supporting the seal will be improved further if the piston head consists of a conical member, which is mounted on the piston skirt and is continued by the flange, and the included angle of the conical member exceeds the included angle of the flange.

The resiliency of the seal of the piston can also be influenced in that the annular seal, in a manner known per se, and optionally also the flange has a smaller wall thickness than the syringe cylinder and the wall thickness of the annular seal preferably decreases in known manner toward its free rim and, in addition, the wall thickness of the flange also decreases toward the annular seal.

In a desirable arrangement, the annular seal is provided in known manner on the outside with peripheral annular sealing beads at both end portions of its cylindrical shape because the linear contact between the sealing beads and the inside surface of the cylinder will result in more uniform and more accurate sealing conditions.

In an embodiment in which the end wall of the syringe cylinder, with the exception of the region adjacent to the needle holder, has an inside surface which conforms to the end face of the piston head, and the needle holder is eccentrically disposed in the generally triangular space between the flange and the annular seal and interrupts the opposing generally triangular portion of the end wall of the cylinder, the residual volume remaining in the syringe after the injecting operation will be minimized and the removal of inleaked air before an injecting operation will be facilitated.

DETAILED DESCRIPTION OF THE PREFERRED EMBODIMENT

Figure 1:
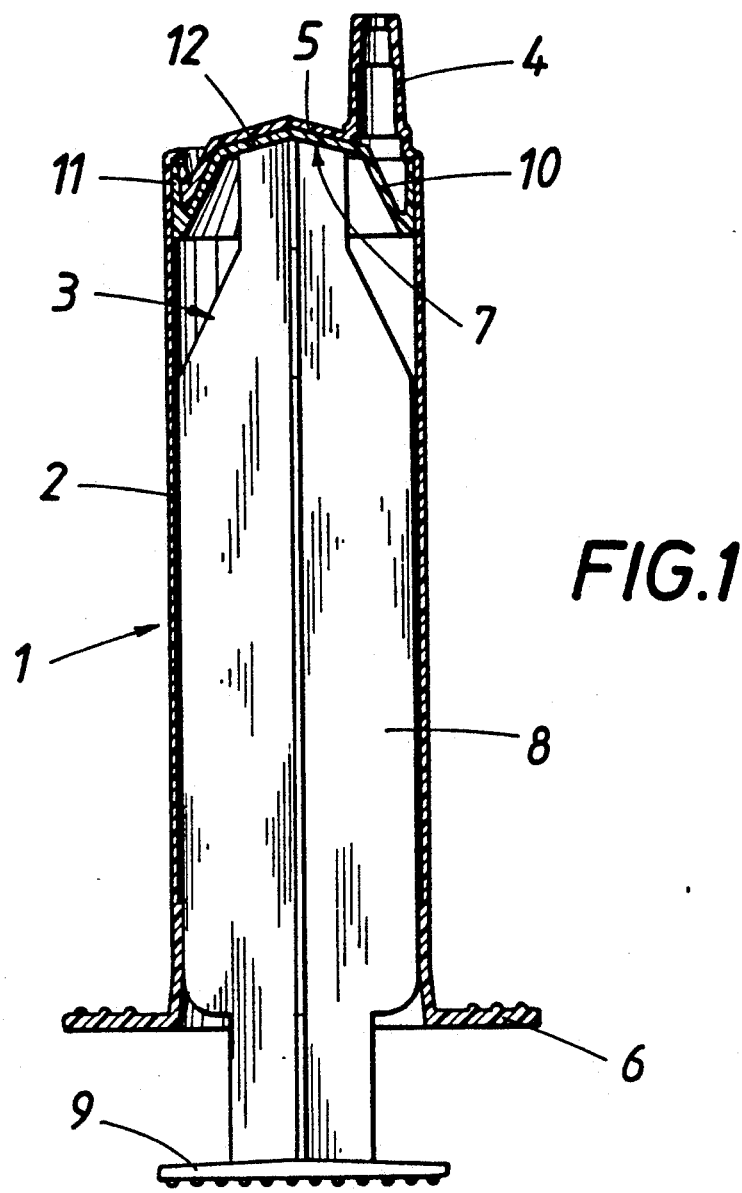
FIGS. 1 and 2 are, respectively, an axial sectional view and an end elevation showing a disposable syringe in accordance with the invention.
Figure 2:
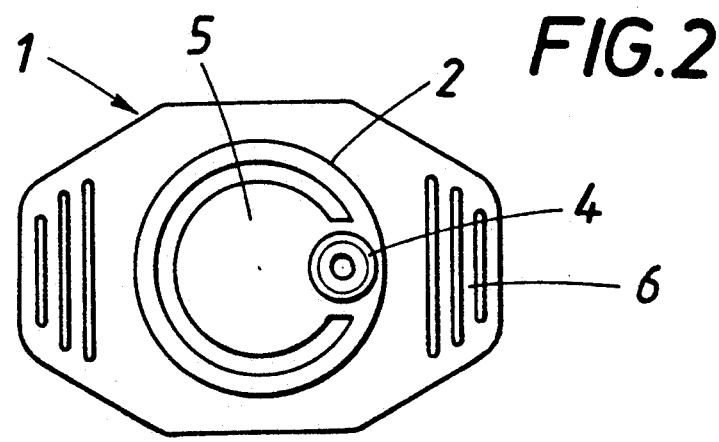
Figure 3:
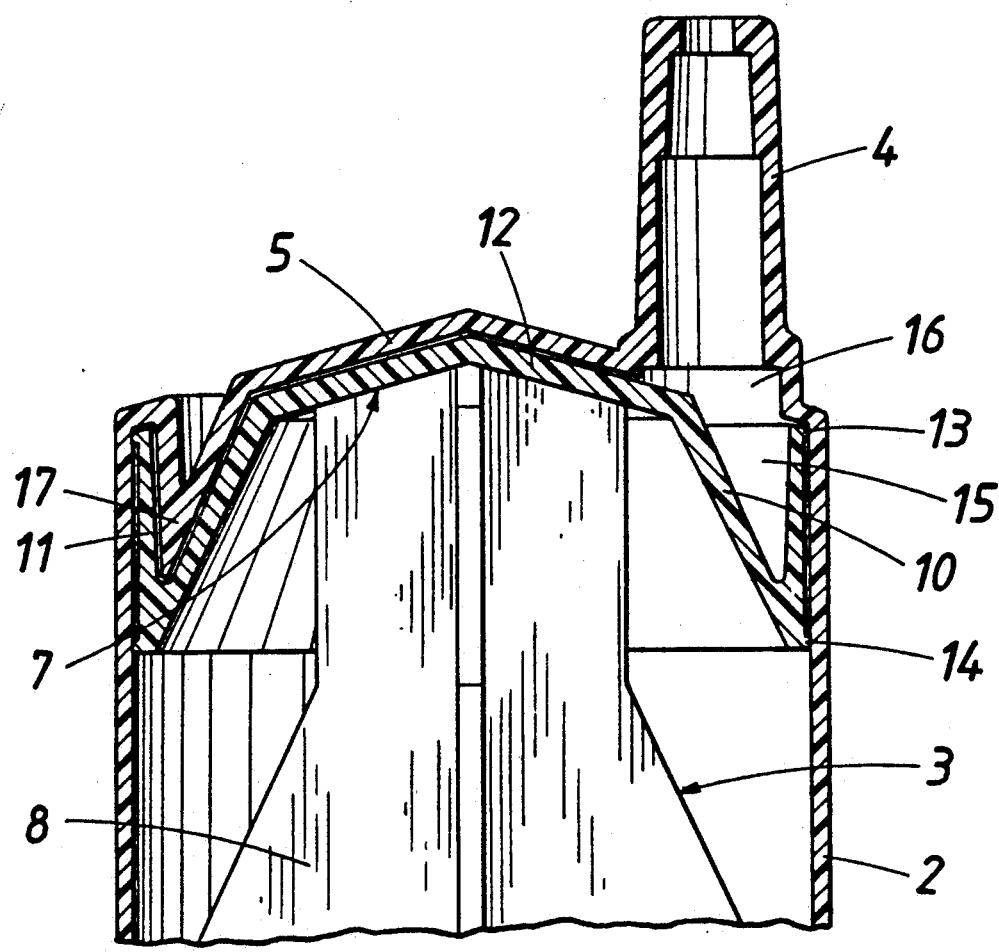
FIG. 3 is an axial sectional view showing on a larger scale as a detail the forward end of that disposable syringe.

An illustrative embodiment of the invention will now be described in more detail with reference to the schematic drawing.

A disposable syringe 1 is composed of a syringe cylinder 2 and a syringe piston 3. The syringe cylinder 2 and the syringe piston 3 consist each of a single piece made of a synthetic thermoplastic material. The syringe cylinder 2 comprises at one end an end wall 5, which is closed with the exception of the region adjacent to a hollow needle holder 4. At its other end, the syringe cylinder 2 constitutes a handle 6. The syringe piston 3 comprises a piston head 7 and a piston skirt 8, which at its free end protruding from the syringe cylinder 2 comprises a handle 9. The piston head 7 is provided with a flange 10, which carries an annular seal 11 that contacts the inside surface of the cylinder. The flange 10 has a frustoconical inside surface, which faces the piston skirt 8 and the open end of the syringe cylinder 2, and a frustoconical outside surface, which faces the inside surface of the syringe cylinder 2 and the end wall 5 of said cylinder. The flange 10 flares toward the open end of the syringe cylinder 2. The annular seal consists of a cylinder, which freely protrudes from the flange toward the end wall 5. The piston head 7 comprises a conical member 12, which is mounted on the piston skirt 8 and is continued by the flange 10 but has a much larger included angle than said flange. The two end portions of the cylindrical annular seal 11 are formed on the outside with peripheral annular sealing beads 13, 14 in sealing contact with the inside surface of the cylinder. Besides, the end wall 5 of the syringe cylinder 2, with the exception of the region adjacent to the needle holder, has an inside surface which conforms to the end face of the piston head. The needle holder 4 is eccentrically disposed in the peripheral annular space 15 that is defined by the flange 10 and the annular seal 11 and is generally triangular in radial section. The needle holder 4 has an opening 16, which intersects the peripheral annular portion 17 that is formed in the end wall of the cylinder and is generally triangular in radial section.

The special design of the syringe piston 3 provides a resilient, soft piston seal, which ensures an absolutely tight contact between the piston and the cylinder and nevertheless permits the syringe to be actuated easily. The pressure conditions occurring in the syringe cylinder 2 will influence the contact pressures exerted between the annular seal 11 and the syringe cylinder 2 and will cause said forces to match the prevailing pressure conditions. For instance, the injection operation will cause an overpressure to be built up in the generally triangular space 15 adjacent to the piston head 7 so that a force will be exerted which urges the annular seal 11 radially outwardly and the sealing bead 13 at the free end portion of the seal will be forced more strongly against the inside surface of the cylinder so as to ensure a tight seal. During the intake operation the negative pressure being built up in the generally triangular space 15 will act on the flange 10 so that the sealing bead 14 at the other end portion of the seal 11 will be strongly forced against the inside surface of the cylinder and a tight seal will thus be ensured also during the intake stroke.

Even variations of the diameter of the syringe cylinder 2 as a result of an expansion of said cylinder or a canting of the syringe piston 3 during an actuation of the syringe will readily be taken up and compensated without any risk of a leak by the resiliency and compliance of the annular seal 11.

Because the end face of the piston head and the inside surface of the end wall conform to each other, the residual volume left after an injection operation will be minimized and that conformity and the eccentric arrangement of the needle holder will facilitate the escape of inleaked air because any air bubbles will migrate along the generally triangular space 15 into the opening 16 of the holder so that such bubbles can reliable be ejected.

I claim:

1. A disposable syringe comprising a syringe cylinder having an inside peripheral surface, an open first end and a second end, an end wall at said second end, the end wall being provided with a hollow needle holder and being closed with the exception of the region adjacent to said needle holder, a syringe piston comprising a piston skirt that protrudes out of said open first end of said cylinder and is provided with a handle outside said cylinder, and a piston head disposed within said cylinder and facing said second end thereof, the piston head having an end face facing said second cylinder end and carrying a peripheral annular flange that is provided with an annular seal in sliding contact with said inside peripheral surface of said cylinder, said end wall of said cylinder having an inside surface which, except adjacent to said needle holder, conforms to said end face of said piston head, said flange having a frustoconical inside surface facing said first end of said cylinder and said piston skirt and a frustoconical outside surface facing said inside peripheral surface of said cylinder and said second end of said cylinder, said flange flaring toward said first end of said cylinder, said inside surface of said flange and said annular seal defining a peripheral annular space which is generally triangular in radial section, said end wall of said cylinder comprising a peripheral annular portion which is generally triangular in radial section and conforms to said annular space, said needle holder being eccentrically disposed with respect to said end wall and extending through said annular portion and opening into said annular space, the radical distance from said frustoconical inside surface to said piston skirt continuously increasing toward said second end of said cylinder, and said annular seal being cylindrical and being joined to, and coaxial with, said flange and freely protruding therefrom toward said end wall of said cylinder.

2. The syringe set forth in claim 1, wherein said annular seal has a smaller wall thickness than said cylinder and decreases toward said annular seal.

3. The syringe set forth in claim 1, wherein said flange has a smaller wall thickness than said cylinder.

* * * * *